United States Patent
Harms et al.

(10) Patent No.: US 10,406,015 B2
(45) Date of Patent: Sep. 10, 2019

(54) PATIENT STABILIZATION AND TRANSPORT AID

(71) Applicant: X-CEN-TEK GmbH & Co. KG, Wardenburg (DE)

(72) Inventors: Andreas Harms, Ofen (DE); Thomas Busch, Wardenburg (DE)

(73) Assignee: X-CEN-TEK GmbH & Co. KG, Wardenburg (DE)

( * ) Notice: Subject to any disclaimer, the term of this patent is extended or adjusted under 35 U.S.C. 154(b) by 386 days.

(21) Appl. No.: 14/711,040

(22) Filed: May 13, 2015

(65) Prior Publication Data
US 2015/0328037 A1   Nov. 19, 2015

(30) Foreign Application Priority Data
May 13, 2014   (DE) .......... 10 2014 106 734

(51) Int. Cl.
*A61F 5/055* (2006.01)
*A61F 5/37* (2006.01)

(52) U.S. Cl.
CPC ............ *A61F 5/055* (2013.01); *A61F 5/3707* (2013.01)

(58) Field of Classification Search
CPC .... A61F 5/05; A61F 5/055; A61F 5/37; A61F 5/3707; A41B 13/06; A41D 23/00
USPC .......... 602/18; 128/869, 876; 2/207
See application file for complete search history.

(56) References Cited

U.S. PATENT DOCUMENTS

| | | | | | |
|---|---|---|---|---|---|
| D109,690 | S | * | 5/1938 | Atwood | D2/500 |
| 2,221,155 | A | * | 11/1940 | Stone | A42B 1/041 2/171.02 |
| 2,538,420 | A | * | 1/1951 | Junghans | A41B 13/06 2/69 |
| 2,600,814 | A | * | 6/1952 | Tomarkin | A41D 23/00 2/207 |
| 3,036,450 | A | * | 5/1962 | Holder | A42B 1/045 2/206 |
| 4,993,080 | A | * | 2/1991 | Doty | A41D 23/00 2/181 |
| 5,058,211 | A | * | 10/1991 | Hanks | A41D 23/00 128/201.13 |
| 5,211,623 | A | * | 5/1993 | Sarkozi | A61F 5/055 128/DIG. 23 |
| 5,637,067 | A | * | 6/1997 | Ausmus | A63B 21/0004 482/140 |
| 5,921,903 | A | * | 7/1999 | Lawrence | A63B 23/0211 482/131 |

(Continued)

FOREIGN PATENT DOCUMENTS

DE   19547115 A1   6/1997

*Primary Examiner* — Keri J Nelson
(74) *Attorney, Agent, or Firm* — Renner, Otto, Boisselle & Sklar, LLP

(57) ABSTRACT

The invention relates to a patient stabilization and transport aid (1) having two triangular sections (3, 4) made of a flexible material, wherein the sections (3, 4) are attached to one another along a connecting line (5) on one side (A) of the triangle, wherein a handle-reinforcing strip (6), in particular in the form of a belt band, is engaged in a releasable connection (7, 8) with the triangular sections (3, 4) along the connecting line (5), and handle loops (91, 92) are present on the ends (61, 62) of the handle-reinforcing strip (6) protruding beyond the tips (21 and 22; 31 and 32) of the triangular sections (2, 3).

8 Claims, 4 Drawing Sheets

(56) References Cited

U.S. PATENT DOCUMENTS

Figure 1:
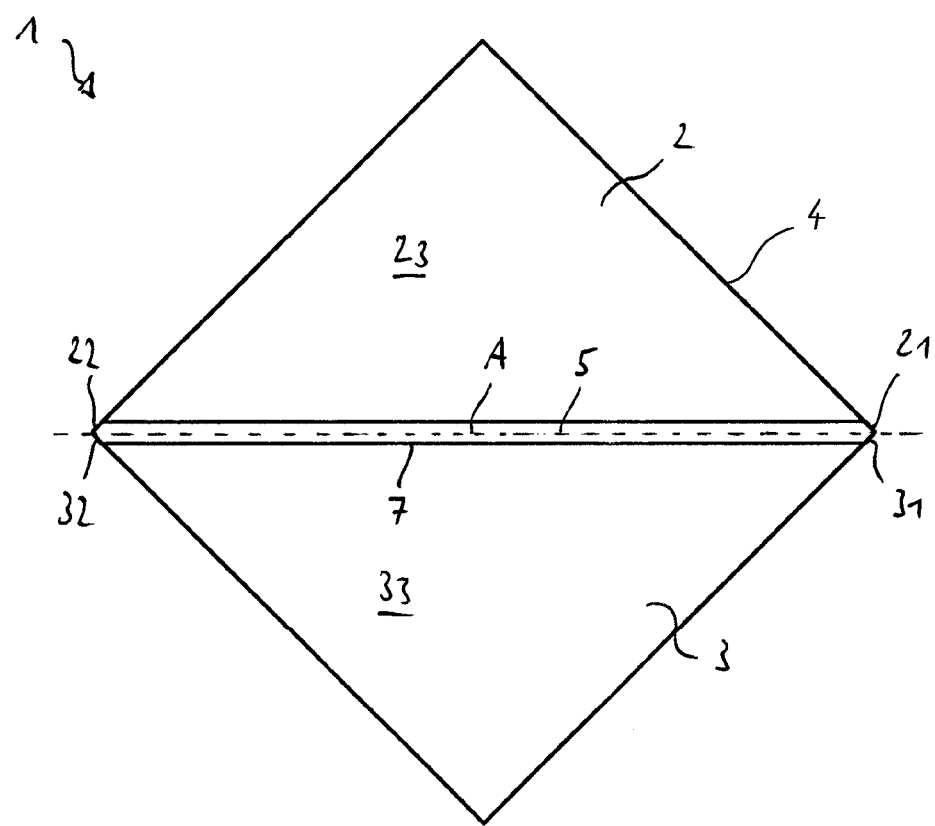

| | | | | |
|---|---|---|---|---|
| 6,032,292 A * | 3/2000 | Wood | ............... | A41D 23/00 |
| | | | | 2/206 |
| 6,644,318 B1 * | 11/2003 | Adams | ............... | A61F 5/055 |
| | | | | 128/869 |
| 7,636,953 B2 * | 12/2009 | Grey | ............... | A41D 23/00 |
| | | | | 2/174 |
| 7,927,311 B1 * | 4/2011 | Bachelder | ............ | A45F 5/00 |
| | | | | 224/148.4 |
| 8,185,969 B2 * | 5/2012 | Chang | ............... | A41D 23/00 |
| | | | | 2/206 |

* cited by examiner

PATIENT STABILIZATION AND TRANSPORT AID

This application claims priority of German Application No. 10 2014 106 734.7 filed May 13, 2014, which is hereby incorporated by reference.

The invention relates to a patient stabilization and transport aid.

In particular in accidents, when the extent of a patient's injuries is not yet known when they are rescued, an attempt is made to restrict any movement of the head and neck area as much as possible. This is usually accomplished by using neck braces, which are relatively difficult to apply.

In addition, there is the known wrapping technique, in which a rolled-up cloth can be wrapped skillfully around a patient's neck and shoulders, thus also facilitating fixation.

It is unfavorable here that rolling up the wrap may often be unsuccessful under the conditions of actual use, and wrapping the rolled-up cloth around a patient can easily result in unintentional rolling.

The object of the invention is to make available an improved patient stabilization and transport aid with which reliable handling is made possible.

This object is achieved by a patient stabilization and transport aid according to the features of claim 1.

According to the invention, a patient stabilization and transport aid is provided, having two triangular sections of a flexible material, the sections being joined to one another along a connecting line on one side of the triangle, wherein a handle-reinforcing strip, in particular in the form of a belt, is engaged in a releasable connection with the triangular sections along the connecting line, and handle loops protruding beyond the tips of the triangular sections are provided at the ends of the handle-reinforcing strip.

In this way a type of reliable winding spindle is supplied by the handle-reinforcing strip in a particularly effective manner, and a handle for facilitated wrapping is provided by the handle loops on the end of the spindle. The releasable connection in turn permits a space-saving stowage of the components before and after use.

An advantageous refinement of the invention provides that the releasable connection consists of a Velcro-type loop material and a hook material between the region of the connecting line and the handle-reinforcing strip.

A reinforcing strip, in particular in the form of a belt, is advantageously applied or sewn on the side of the triangular sections opposite the Velcro-type closure, in particular in the form of a belt.

One variant of the invention provides that the triangular sections are joined to one another in one piece.

Each of the triangular sections preferably forms an obtuse triangle.

An advantageous variant of the invention provides that the triangular sections are made of fleece. These are advantageously not bordered on their edges that are not shared in common.

According to another refinement of the invention, the handle loops consist of a loop strip and are attached or sewn on both sides of the handle-reinforcing strip in particular.

Consequently, it is now being proposed that the loop strip should be twisted once from the top side to the bottom side of the handle-reinforcing strip.

According to a particularly advantageous and therefore preferred embodiment of the invention, a tubular outer cover is provided, into which the triangular sections rolled around the handle-reinforcing strip can be pulled over the corners. This then reliably prevents the triangular sections from rolling up unintentionally on the patient.

Additional advantageous embodiments are derived from the additional dependent claims or their possible combinations among one another.

Figure 2:
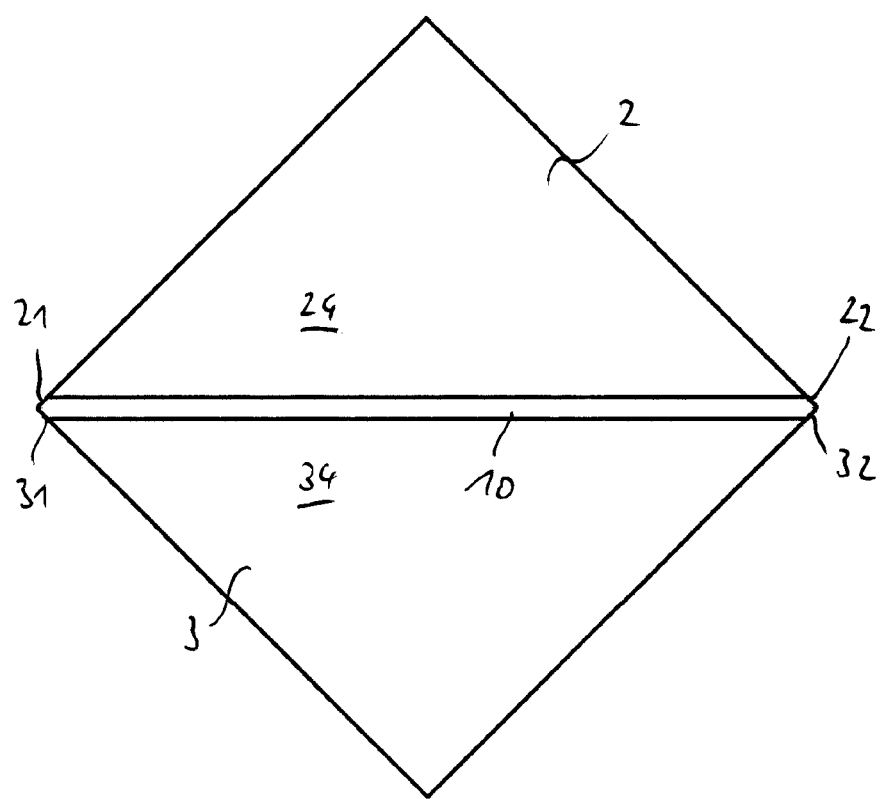
Figure 3:
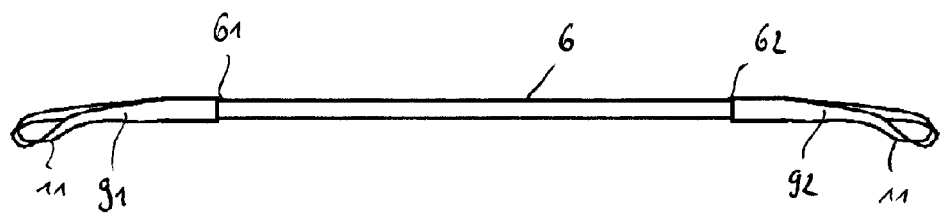
Figure 4:
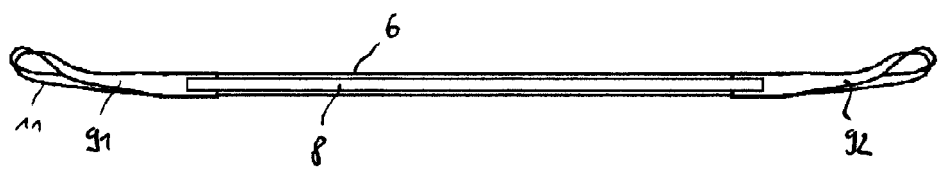
Figure 5:
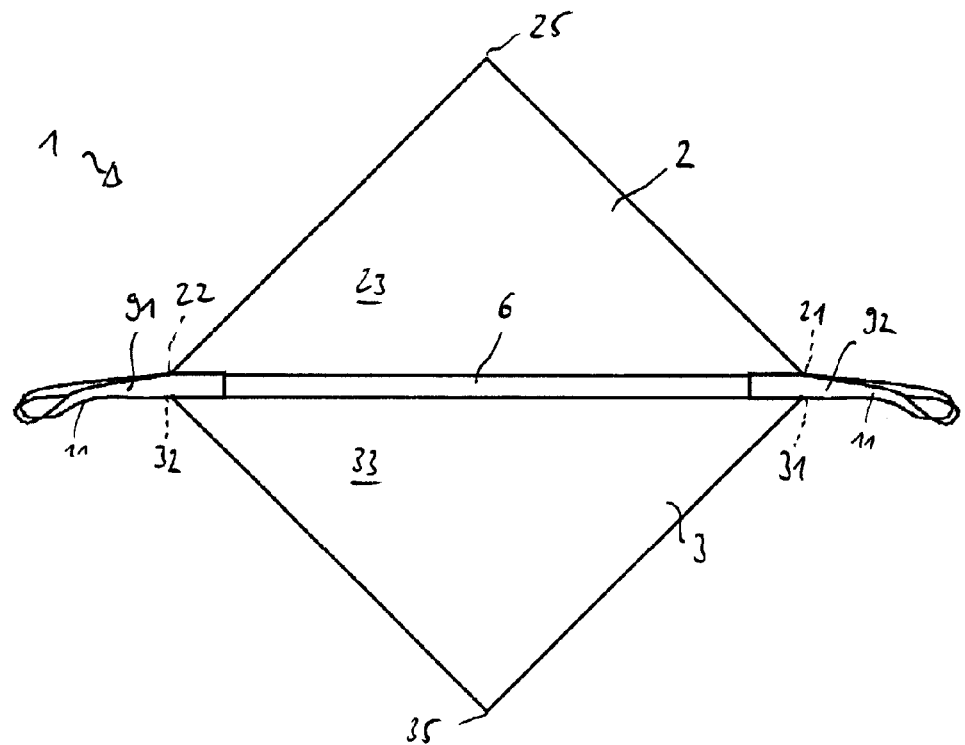
Figure 6:
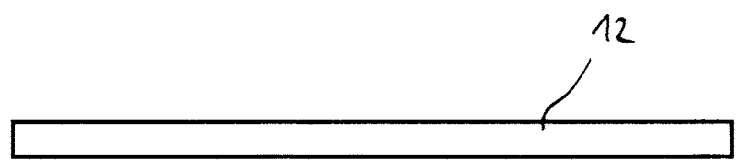
Figure 7:
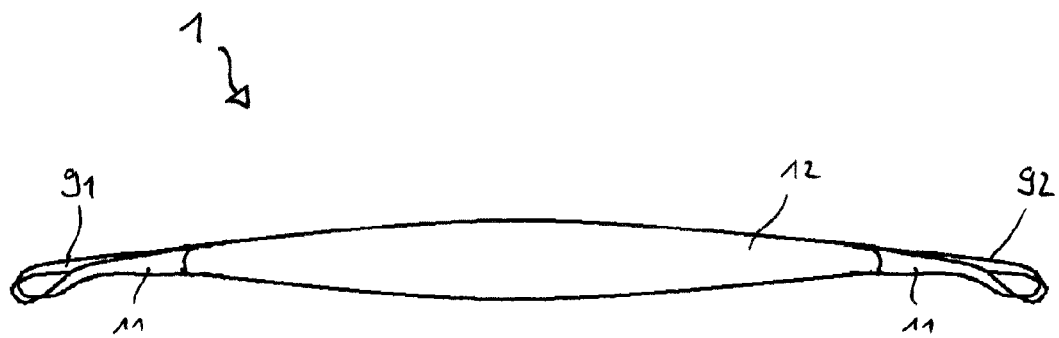

The invention is explained in greater detail below on the basis of the drawings. The schematic diagrams show in particular:

FIG. 1 a schematic diagram of two triangular sections of a flexible material having a loop strip, FIG. 2 the two triangular sections from FIG. 1, as seen from the other side, showing a reinforcing strip opposite the loop strip, FIG. 3 a handle-reinforcing strip having handle loops on the ends, FIG. 4 the handle-reinforcing strip from FIG. 3, showing a hook strip on the underside thereof, FIG. 5 the patient stabilization and transport aid according to the invention in the unrolled condition, FIG. 6 an outer cover, and FIG. 7 the patient stabilization and transport aid according to the invention in the rolled-up state with the outer cover pulled over it.

The same reference numerals in the figures denote the same elements or elements having the same effect.

FIG. 1 shows a schematic diagram of two triangular sections 2 and 3 made of a flexible material 4, namely pieces of fleece fabric sewn together along a connecting line 5 on one triangular side A. In addition to the seam, a loop strip 7 has been sewn onto the seam and/or the region next to the seam. This may also be an adhesive connection.

A reinforcing strip 10 in the form of a belt band is sewn to the hook-and-loop strip 7 on the side 23, 33 of the hook-and-loop connection along the connecting line 5 arranged on the opposite side 24, 34 of the triangular sections 2, 3 according to FIG. 2. The reinforcing strip 10 serves to provide reinforcement.

The triangular sections 2 and 3 may also be designed in one piece.

In the example shown here, each triangular section 2 and 3 forms an obtuse triangle.

FIG. 3 shows a handle-reinforcing strip 6, likewise in the form of a belt band, as seen from above, which cooperates according to the invention with the loop strip 7 on the cloth. Handle loops 91 and 92, having been twisted once from the top side to the bottom side of the handle-reinforcing strip 6, and each consisting of a loop strip 11, are sewn on both sides of the handle-reinforcing strip 6 on the ends 61 and 62 of the handle-reinforcing strip 6.

FIG. 4 shows the bottom side of the handle-reinforcing strip 6 with the hook strip 8 attached to this side, completing the releasable connection between the handle-reinforcing strip 6 and the triangular sections 2, 3.

FIG. 5 shows how the closed hook-and-loop connection functions.

The handle loops 91 and 92 protrude beyond the tips 21 and 22 as well as 31 and 32 of the triangular sections 2 and 3 of the flexible material.

The cloth comprised of the two triangular sections 2 and 3 can then be wound over the tips 35 and/or 25 around the handle-reinforcing strip 6, thus resulting in the desired meandering form.

FIG. 6 shows a tubular outer cover 12, around which it is possible to pull the triangular sections 2 and 3, which are rolled around the handle-reinforcing strip 6, as shown in FIG. 7.

LIST OF REFERENCE NUMERALS 1 patient stabilization and transport aid
2 triangular section
21, 22 tip
23 side of the hook-and-loop connection
24 side opposite the hook-and-loop connection
25 corner
3 triangular section
31, 32 tip
33 side of the hook-and-loop connection
34 side opposite the hook-and-loop connection
35 corner
4 flexible material
5 connecting line
6 handle-reinforcing strip
61, 62 end
7 loop material
8 hook material
91, 92 handle loop
10 reinforcing strip
11 loop strip
12 outer cover
A triangular side

The invention claimed is:

1. A patient stabilization and transport aid comprising:
two triangular sections made of a flexible cloth material, wherein the triangular sections are connected to one another along a connecting line on one side of each of the triangular sections, each of the triangular sections having tips at ends of the connecting line;
a reinforcing strip that extends along a first side of the triangular sections from the first end of the connecting line to the second end of the connecting line;
a handle-reinforcing strip releasably connected to a second side of the triangular sections opposite the first side along the connecting line by a hook-and-loop connection, which is strip-shaped, and consists of a loop material and a hook material between a region of the connecting line and the handle-reinforcing strip, the handle-reinforcing strip being in the form of a belt band that forms a winding spindle for the triangular sections; and
handle loops protruding beyond the tips of the triangular sections and provided on the ends of the handle-reinforcing strip, wherein the handle loops are rotatable to wind the triangular sections around the spindle.

2. The patient stabilization and transport aid according to claim 1, wherein the reinforcing strip is in the form of a belt band and is applied or sewn to the first side of the triangular sections and along the connecting line opposite to where the hook-and-loop connection is placed.

3. The patient stabilization and transport aid according to claim 1, wherein the triangular sections are joined to one another in one piece.

4. The patient stabilization and transport aid according to claim 1, wherein the triangular sections each form an obtuse triangle.

5. The patient stabilization and transport aid according to claim 1, wherein the triangular sections are made of fleece.

6. The patient stabilization and transport aid according to claim 1, wherein the handle loops consist of a loop strip and are applied or sewn to both sides of the handle-reinforcing strip.

7. The patient stabilization and transport aid according to claim 6, wherein the loop strip is twisted once from the top side to the bottom side of the handle-reinforcing strip.

8. The patient stabilization and transport aid according to claim 1, wherein a tubular outer cover is provided, into which the rolled-up triangular sections can be pulled around the handle-reinforcing strip.

* * * * *